United States Patent
Yamamoto et al.

(10) Patent No.: US 10,059,976 B2
(45) Date of Patent: Aug. 28, 2018

(54) MICROORGANISM DETECTION METHOD

(71) Applicant: TSUMURA & Co., Minato-ku (JP)

(72) Inventors: Hiroaki Yamamoto, Ibaraki (JP); Isao Fukuda, Ibaraki (JP)

(73) Assignee: TSUMURA & Co., Minato-ku (JP)

(*) Notice: Subject to any disclaimer, the term of this patent is extended or adjusted under 35 U.S.C. 154(b) by 189 days.

(21) Appl. No.: 14/766,834

(22) PCT Filed: Jun. 10, 2014

(86) PCT No.: PCT/JP2014/065313
§ 371 (c)(1),
(2) Date: Aug. 10, 2015

(87) PCT Pub. No.: WO2015/029539
PCT Pub. Date: Mar. 5, 2015

(65) Prior Publication Data
US 2016/0002697 A1  Jan. 7, 2016

(30) Foreign Application Priority Data
Aug. 30, 2013  (JP) .................. 2013-179920

(51) Int. Cl.
*C12Q 1/04* (2006.01)
*C12Q 1/22* (2006.01)
(Continued)

(52) U.S. Cl.
CPC .............. *C12Q 1/045* (2013.01); *C12Q 1/06* (2013.01); *C12Q 1/22* (2013.01); *G01N 1/405* (2013.01)

(58) Field of Classification Search
None
See application file for complete search history.

(56) References Cited

U.S. PATENT DOCUMENTS 4,543,328 A    9/1985  Keller et al.
2009/0239256 A1*  9/2009  Giglio .................. C12Q 1/04
                                                           435/34
(Continued)

FOREIGN PATENT DOCUMENTS

GB    2 024 421 A    1/1980
JP    6 226092       8/1994
WO    2008 038625    4/2008

OTHER PUBLICATIONS

Extended European Search Report dated Mar. 17, 2017 in Patent Application No. 14840357.9.
(Continued)

*Primary Examiner* — Robert J Yamasaki
*Assistant Examiner* — Charles Zoltan Constantine
(74) *Attorney, Agent, or Firm* — Oblon, McClelland, Maier & Neustadt, L.L.P.

(57) ABSTRACT

Provided is a microorganism detection method which is highly versatile and applicable to both the test for the detection of specified microorganisms and the microbial enumeration test under the same test conditions for Kampo extract preparations and crude drugs containing a variety of antimicrobial substances, is able to effectively reduce the influence of antimicrobial substances in a test sample, and may detect target microorganisms with high precision. This method is a microorganism detection method in a test sample having antimicrobial activity, including a step of preparing a sample liquid containing a test sample having antimicrobial activity and a step of culturing a target microorganism in a culture medium, the method including allowing a (meth)acrylic acid ester-based synthetic adsorbent to act on the sample liquid and/or the culture medium.

11 Claims, 1 Drawing Sheet

(51) Int. Cl.
  *C12Q 1/06*  (2006.01)
  *G01N 1/40*  (2006.01)

(56) References Cited

U.S. PATENT DOCUMENTS

2010/0062515 A1    3/2010  Yamamoto
2012/0156295 A1*   6/2012  Mishra .................... C07K 5/10
                                                   424/474

OTHER PUBLICATIONS

L.C.L. Aquino et al., "Adsorption of human immunoglobulin G onto ethacrylate and histidine-linked methacrylate" Brazilian Journal of Chemical Engineering, vol. 20, No. 3, XP55345010, Jan. 1, 2003, pp. 1-21.
Robert V. Slone, "Methacrylic Ester Polymers", Encyclopedia of Polymer Science and Technology, vol. 3, XP002463013, Oct. 22, 2001, pp. 249-277.
International Search Report dated Sep. 9, 2014 in PCT/JP2014/065313 filed Jun. 10, 2014.
Saikia, D. M., "Revisiting adsorption of biomolecules on polymeric resins", Colloids and Surfaces A: Physicochem. Eng. Aspects, vol. 315, No. 1-3, pp. 196-204, 2008.

* cited by examiner

MICROORGANISM DETECTION METHOD

TECHNICAL FIELD

The present invention relates to a microorganism detection method, and in more detail, the present invention relates to a microorganism detection method capable of reducing the influence of antimicrobial substances contained in a test sample and detecting target microorganisms with high precision.

BACKGROUND ART

In the fields of foods, medical and pharmaceutical products, and the like, in order to ensure the quality and safety, the microbiological examination of products or raw materials is carried out. As for test methods thereof, official analytical methods are prescribed in the respective fields, and so far as the medical and pharmaceutical products are concerned, various testing methods for microorganisms are described in the Japanese Pharmacopoeia. Among these, as for nonsterile preparations and raw materials thereof, the microbial limit test is prescribed, and this includes microbial enumeration tests for measuring microbial counts and a test for the detection of specified microorganisms regarding specified pathogenic microorganisms and the like. Furthermore, as for crude drugs, the microbial limit test for crude drugs is prescribed in Chapter 5.02 of the tests for crude drugs of the general tests. However, in the case where the microbial limit test is applied to a Kampo extract preparation and a crude drug that is a raw material thereof, the growth of a target microorganism is inhibited due to the influence of antimicrobial substances (inclusive of antifungal substances, hereinafter the same) contained in the Kampo extract preparation and the crude drug, which becomes problematic for accurate detection of the target microorganism.

In general, the antimicrobial activity of a test sample may be removed by inactivating the antimicrobial activity (neutralization of growth inhibitors), increasing the dilution ratio of a sample liquid, increasing the amount of a medium, membrane filtration, and the like. However, a variety of antimicrobial substances are contained in a Kampo extract preparation and a crude drug that is a raw material thereof, or the like, and thus, it is extremely difficult to effectively inactivate these antimicrobial substances with a specified inactivating agent. For example, by adding lecithin and polysorbate to a medium in a known method for inactivation of antimicrobial substances, a high effect in the inactivation of paraben type or mercury type preservatives or the like is obtained, whereas, in many cases, a sufficient effect in the inactivation of Kampo extract preparations is not obtained. Actually, a crude drug that is a raw material of the Kampo medicine contains a variety of compounds ranging from low-molecular weight compounds to high-molecular weight compounds. The majority of these compounds are characteristic components in view of molecular structures (e.g., terpenoid, alkaloid, flavonoid, quinones, amino acids, fatty acids, sugars, etc.) and contain a lot of antimicrobial substances (e.g., terpenoid, alkaloid, flavonoid, tannins, etc.). A Kampo extract preparation is composed of several species of crude drugs, and thus, it contains a wide range of antimicrobial substances. Furthermore, the Kampo extract preparation contains a lot of insoluble fine particles resulting from a production method thereof, and therefore the membrane filtration which is widely used to remove antimicrobial substances cannot be employed. Meanwhile, increasing the dilution ratio or the amount of a medium can hardly be considered the method of choice, because it leads to a decline in the sensitivity.

In view of these problems, the present applicant has already proposed a method for removing antimicrobial substances in a test sample by adding activated carbon and acid clay or activated clay to a medium (PTL 1). This method is useful in the test for the detection of specified microorganisms; however, in the microbial enumeration test by the plate-count method using an agar medium, it is difficult to discriminate colonies because not only is the medium colored with the activated carbon, but also a degree of transparency of the medium is reduced by the acid clay or activated clay. Furthermore, it is not easy to separate and remove these substances, which leads to difficulties in accurately discriminating and measuring colonies.

CITATION LIST

Patent Literature

PTL 1: WO 2008/038625, pamphlet

SUMMARY OF INVENTION

Technical Problem

Accordingly, there is demand for a microorganism detection method which is highly versatile and applicable to both the test for the detection of specified microorganisms and the microbial enumeration test under the same test conditions for Kampo extract preparations and crude drugs containing a variety of antimicrobial substances, is able to effectively reduce the influence of antimicrobial substances in a test sample, and may detect target microorganisms with high precision. An aim that the present invention is to achieve is to provide such a microorganism detection method.

Solution to Problem

In order to solve the foregoing problem, the present inventors made extensive and intensive investigations. As a result, it has been found that while a (meth)acrylic acid ester-based synthetic adsorbent is able to adsorb and remove a wide range of antimicrobial substances contained in a test sample, it has weak adsorption action against nutritional components necessary for the growth of a target microorganism and does not inhibit the growth of the target microorganism, thereby enhancing the detection precision; and that even when added to a medium, the instant adsorbent does not cause the medium to be colored and may be easily removed after being allowed to act, which makes it possible to carry out precise measurement even in the plate-count method or the like. Thus, the present invention has been completed.

Specifically, the invention is concerned with a microorganism detection method in a test sample having antimicrobial activity, including a step of preparing a sample liquid containing a test sample having antimicrobial activity and a step of incubating a target microorganism in a culture medium, the method is characterized by allowing a (meth)acrylic acid ester-based synthetic adsorbent to act on the sample liquid and/or the culture medium.

Advantageous Effects of Invention

According to the microorganism detection method of the invention, antimicrobial substances contained in the test sample are effectively adsorbed and removed, and thus, the growth of the target microorganism is not inhibited at the time of culture, thereby enabling accurate detection with high precision. In addition, since the influence of a wide range of antimicrobial substances can be reduced, an extended range of microorganisms are targeted for detection; and the microorganism detection method of the invention is applicable to a lot of Kampo extract preparations or crude drugs, which means that the method is applied widely and highly versatile. Furthermore, even when added to a medium, the (meth)acrylic acid ester-based synthetic adsorbent for use in the invention neither colors nor opacifies the medium, and the adsorbent may be easily separated and removed after being allowed to act. Therefore, colonies can be accurately discriminated even by the plate-count method or the like, and it is possible to conduct the measurement rapidly and accurately.

DESCRIPTION OF EMBODIMENTS

Figure 1:
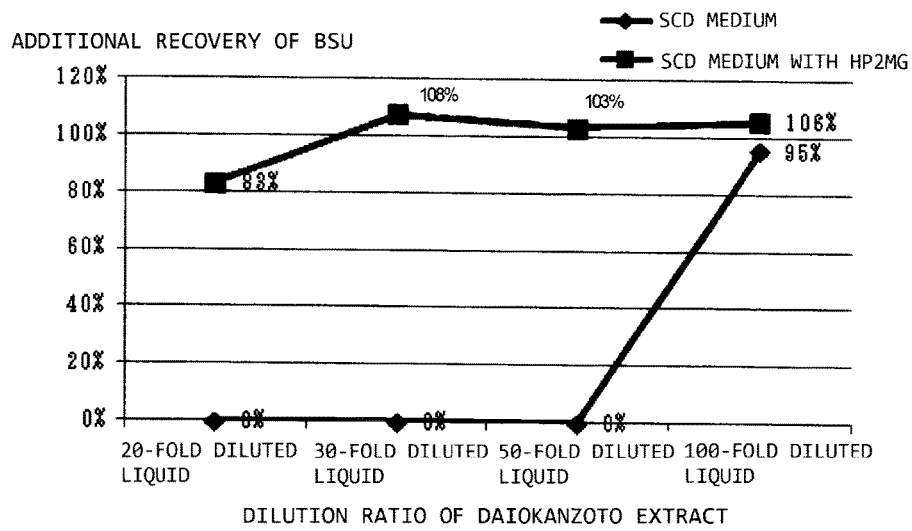
FIG. 1 is a graph plotting an additional recovery of *Bacillus subtilis* with respect to a dilution ratio for Daiokanzoto as a test sample in Example 6.

The method of the invention is a method for detecting microorganisms in a test sample having antimicrobial activity. While this method includes a step of preparing a sample liquid containing a test sample and a step of culturing a target microorganism in a culture medium, it is characterized by allowing a (meth)acrylic acid ester-based synthetic adsorbent to act on either one or both of the sample liquid in the sample liquid preparation step and the culture medium in the culture step.

Examples of the test sample having antimicrobial activity (hereinafter sometimes referred to simply as "test sample") may include Kampo extract preparations, crude drugs, and the like. The Kampo extract preparation is one resulting from formulating an extract component obtained by extracting a Kampo formulation with a water-soluble solvent such as water and ethanol, and its dosage form is not particularly limited. Any form of a powder, a granule, a tablet, a liquid, a pill, a capsule, and the like may be adopted. Kampo medicines are those which have been independently developed after the compounding ratios and standards for use (symptoms) of crude drugs described in medical books written in ancient China were introduced into Japan, and in the Kampo formulations, the kind and compounding ratio of the crude drugs are determined according to the formulation. Specific examples of Kampo formulations may include Kakkonto, Kakkontokasenkyushin'i, Otsujito, Anchusan, Jumihaidokuto, Hachimijiogan, Daisaikoto, Shosaikoto, Saikokeishito, Saikokeishikankyoto, Saikokaryukotsuboreito, Hangeshashinto, Orengedokuto, Hangekobokuto, Goreisan, Keishikajutsubuto, Shoseiryuto, Boiogito, Shohangekabukuryoto, Shofusan, Tokishakuyakusan, Kamishoyosan, Keishibukuryogan, Keishikaryukotsuboreito, Maoto, Eppikajutsuto, Bakumondoto, Shimbuto, Goshuyuto, Ninjinto, Daiobotampito, Byakkokaninjinto, Shigyakusan, Mokuboito, Hangebyakujutsutemmato, Tokishigyakukagoshuyushokyoto, Ryokeijutsukanto, Choreito, Hochuekkito, Rikkunshito, Keishito, Shichimotsukokato, Chotosan, Juzentaihoto, Keigairengyoto, Junchoto, Yokuininto, Sokeikakketsuto, Yokukansan, Makyokansekito, Gorinsan, Unseiin, Seijobofuto, Jizusoippo, Keishikashakuyakuto, Tokakujokito, Bofutsushosan, Goshakusan, Shakanzoto, Kihito, Jinsoin, Nyoshinsan, Shakuyakukanzoto, Bukuryoin, Kososan, Shimotsuto, Kambakutaisoto, Saikanto, Choijokito, Shikunshito, Ryutanshakanto, Kyukikyogaito, Makyoyokukanto, Heisan, Saikoseikanto, Nichinto, Keishininjinto, Yokukansankachimpihange, Daiokanzoto, Shimpito, Tokiinshi, Rokumigan, Nijutsuto, Jidabokuippo, Seihaito, Chikujountanto, Jiinshihoto, Jiinkokato, Gokoto, Saibokuto, Daibofuto, Ogikenchuto, Shokenchuto, Daikenchuto, Shomakakkonto, Tokito, Sansoninto, Shin'iseihaito, Tsudosan, Unkeito, Goshajinkigan, Ninjin'yoeito, Shosaikotokakikyosekko, Rikkosan, Seishinrenshiin, Choreitogoshimotsuto, San'oshashinto, Saireito, Ireito, Bukuryoingohangekobokuto, Inchingoreisan, Ryokyojutsukanto, Ryokankyomishingeninto, Orento, Sammotsuogonto, Hainosankyuto, Tokikenchuto, Senkyuchachosan, Keishibukuryogankayokuinin, Mashiningan, Maobushisaishinto, Keihito, Daijokito, Keishikashakuyakudaioto, Inchinkoto, Seishoekkito, Kamikihito, Kikyoto, and the like. Combinations and compounding ratios of crude drugs of those Kampo formulations are described in *Kampo Iyakuhin Shu* (edited by Japan Pharmaceutical Information Center, published in 2011), *The guide book of the approval standards for OTC Kampo products (revised edition)* (supervised by Society of Japanese Pharmacopoeia and edited by Japan Kampo Medicines Manufacturers Association, published in 2009), and the like.

Crude drugs are those prepared by processing medicinal parts obtained from plants or animals, cell inclusions and secretes separated from the origins, their extracts, and minerals by washing, peeling, cutting, drying, sorting, or the like. Specific examples thereof include Donkey Glue, Gambir, Anise Seed, Clematis Root, Artemisia Capillaris Flower, Epimedium Herb, Fennel, Lindera Root, Corydalis Tuber, Astragalus Root, Scutellaria Root, Phellodendron Bark, Cherry Bark, Coptis Rhizome, Polygala Root, Artemisia Leaf, Myrobalan Fruit, Polygonum Root, Pueraria Root, Aluminum Silicate Hydrate with Silicon dioxide, Cutch, German Chamomile Flower, Trichosanthes Root, Trichosanthes Seed, Processed Ginger, *Glycyrrhiza*, Platycodon Root, Immature Orange, Chrysanthemum Flower, Japanese Valerian, Notopterygium, Apricot Kernel, Lonicera Flower, Lycium Fruit, Sophora Root, Schizonepeta Spike, Cinnamon Bark, Cassia Seed, Geranium Herb, Koi, Safflower, Cyperus Rhizome, Brown Rice, Magnolia Bark, Oriental Bezoar, Achyranthes Root, Euodia Fruit, Burdock Fruit, Sesame, *Schisandra* Fruit, Bupleurum Root, Asiasarum Root, Crataegus Fruit, Gardenia Fruit, Cornus Fruit, Zanthoxylum Fruit, Jujube Seed, Dioscorea Rhizome, Rehmannia Root, Lycium Bark, Lithospermum Root, Tribulus Fruit, Prepared *Glycyrrhiza*, Peony Root, Plantago Seed, Plantago Herb, *Eupolyphaga*, Houttuynia Herb, Amomum Seed, Ginger, *Schisandra Repanda*, Wheat, Sweet Flag Root, Cimicifuga Rhizome, Magnolia Flower, Malted Rice, Abalone Shell (Sea-ear Shell), Gypsum, Cnidium Rhizome, Phododendori Folium (Leaf), Senega, Peucedanum Root, Nuphar Rhizome, Cicada Slough, Senna Leaf, *Atractylodes Lancea* Rhizome, *Gleditsia Sinensis* Spine, Mulberry Bark, Mulberry Root-Bark, Sappan Wood, Perilla Herb, Rhubarb, Jujube, Alisma Rhizome, Bamboo Culm, *Panax Japonicus* Rhizome, Anemarrhena Rhizome, Green Tea Leaf, Clove, Uncaria Hook, *Polyporus Sclerotium*, Citrus Unshiu Peel, Arisaema Tuber, Gastrodia Tuber, Asparagus Tuber, Bitter Orange Flower, Benincasa Seed, Japanese Angelica Root, Bitter Orange Peel, Peach Kernel, Swertia Herb, Aralia Rhizome, Eucommia Bark, Animal Gall, Ginseng, Lonicera Leaf And Stem, Fritillaria Bulb, Malt, Ophiopogon Tuber, Croton Seed, Mentha Herb, Glehnia Root And Rhizome, Pinellia Tuber, Lilium Bulb, *Angelica Dahurica* Root, *Atractylodes* Rhizome, Loquat Leaf, *Areca, Poria Sclerotium*, Processed Aconite Root, Specific Processed Aconite Root, Powdered Processed Aconite Root, Sinomenium Stem And Rhizome, Imperata Rhizome, Mirabilite, Saposhnikovia Root And Rhizome, Quercus Bark, Moutan Bark, Hop Strobile, Oyster Shell, Ephedra Herb, Hemp Fruit, Melissa (Herb), Akebia Stem, Cocculus Root, Saussurea Root, Bitter Cardamon, Leonurus Herb, Bear Bile, Coix Seed, Lavender Flower, Longan Aril, Longgu, Japanese Gentian, *Alpinia Officinarum* Rhizome, Forsythia Fruit, Nelumbo Seed, Aralia Root, and the like, with Rhubarb, *Glycyrrhiza*, and Coptis Rhizome being especially useful.

A sample liquid containing the above test sample is prepared. In the case where the test sample is a liquid, this may be used directly as the sample liquid. In the case where the test sample is a solid, the sample liquid is prepared by treating the test sample by means of pulverization, crushing, grinding, or the like, as needed, followed by suspending in an appropriate diluted liquid. Though the diluted liquid is not particularly limited, a buffer solution such as a buffered sodium chloride-peptone solution and phosphoric acid buffer solution, a liquid medium, and the like, as described in the Japanese Pharmacopoeia 16th edition (revised edition) (see General Tests, Chapter 4.05: Microbial Limit Test and Chapter 5.02: Microbial Limit Test for Crude Drugs, hereinafter the same) are suitably used. Examples of the liquid medium include a fluid soybean-casein digest medium (hereinafter abbreviated as "SCD medium"), a fluid sabouraud glucose medium, and the like. From the viewpoints of sensitivity, accuracy, and the like of the measurement, the dilution ratio is preferably 10 to 1,000 times, more preferably 10 to 60 times, still more preferably 10 to 30 times, and especially preferably 10 to 20 times.

The thus-prepared sample liquid is added to the culture medium to incubate a target microorganism. In the case of using a liquid medium such as an SCD medium, as the diluted liquid, it may be used directly as a culture medium without being added to another culture medium. The culture medium is not particularly limited, and for example, the media described in the Japanese Pharmacopoeia may be properly chosen according to the kind of a target microorganism for detection, or the like. Specifically, examples thereof include soybean-casein digest agar medium (hereinafter abbreviated as "SODA medium"), soybean-casein digest agar medium with lecithin and polysorbate 80 (hereinafter abbreviated as "SCDLPA medium"), sabouraud dextrose (glucose) agar medium (hereinafter abbreviated as "SDA medium"), potato dextrose agar medium (hereinafter abbreviated as "PDA medium"), glucose peptone agar medium (hereinafter abbreviated as "GPA medium"), and the like. Though the culture condition is properly set up according to the kind of a target microorganism, or the like, it may be, for example, set up in conformity with the microbial limit test of the Japanese Pharmacopoeia.

In the method of the invention, a (meth)acrylic acid ester-based synthetic adsorbent is allowed to act on the sample liquid and/or the culture medium. It is to be noted that the "(meth)acrylic acid" in this specification means acrylic acid and/or methacrylic acid. Though the (meth) acrylic acid ester-based adsorbent is not particularly limited, its modal pore radius (in a dry form) is preferably 50 to 1,000 angstrom, and more preferably 50 to 500 angstrom. Its specific surface area is preferably 100 to 700 $m^2/g$, and more preferably 130 to 570 $m^2/g$; and its pore volume is preferably 0.4 to 1.5 mL/g, and more preferably 0.5 to 1.3 mL/g. These ranges are preferable because a selective adsorption action against an antimicrobial substance and an effect in suppressing the growth inhibition of a microorganism are enhanced. Examples of commercially available products of the (meth)acrylic acid ester-based adsorbent may include DIAION (registered trademark) HP2MG (manufactured by Mitsubishi Chemical Corporation, modal pore radius=240 angstrom, specific surface area=570 $m^2/g$, pore volume=1.3 mL/g), LEWATIT (registered trademark) VPOC1600 (manufactured by LANXESS K.K., modal pore radius=75 angstrom, specific surface area=130 $m^2/g$, pore volume=0.5 mL/g), PuroSorb PAD950 (manufactured by Purolite K.K., modal pore radius=500 to 1,000 angstrom, specific surface area=535 $m^2/g$, pore volume=1.3 mL/g), Amberlite™ XAD™ 7HP (manufactured by Organo Corporation, modal pore radius=50 angstrom, specific surface area=500 $m^2/g$, pore volume=0.6 mL/g), and the like.

The method for allowing the (meth)acrylic acid ester-based synthetic adsorbent to act on the sample liquid and/or the culture medium is not particularly limited and may be conducted through bringing the sample liquid and/or the culture medium into contact with the (meth)acrylic acid ester-based synthetic adsorbent. For example, in the case of allowing the (meth)acrylic acid ester-based synthetic adsorbent to act on the sample liquid, the adsorbent may be added in the sample liquid as prepared above. Specifically, the (meth)acrylic acid ester-based synthetic adsorbent may be added to the diluted liquid together with the test sample, or the test sample may be added to the diluted liquid having the (meth)acrylic acid ester-based synthetic adsorbent added thereto in advance, so that the sample liquid may contain the (meth)acrylic acid ester-based synthetic adsorbent. In this way, by allowing the (meth)acrylic acid ester-based synthetic adsorbent to act on the test sample-containing sample liquid, the antimicrobial substance eluted from the test sample is adsorbed onto the (meth)acrylic acid ester-based synthetic adsorbent and removed. In addition, by stirring and mixing the sample liquid containing the test sample and the (meth)acrylic acid ester-based synthetic adsorbent for a prescribed time, the antimicrobial substance may be more efficiently adsorbed and removed. Though the stirring and mixing time is not particularly limited, the sample liquid may be, for example, stirred and mixed for about 10 to 60 minutes. A content of the (meth)acrylic acid ester-based synthetic adsorbent in the sample liquid is preferably 3 to 20% by mass, and more preferably 5 to 10% by mass. When the content of the (meth)acrylic acid ester-based synthetic adsorbent falls within this range, favorable detection precision is obtained, and pipette handling properties are not affected. After acting on the sample liquid in this way, though the (meth)acrylic acid ester-based synthetic adsorbent may be allowed to remain as it is, this may also be separated and removed from the sample liquid. A separation and removal method is not particularly limited, and the (meth)acrylic acid ester-based synthetic adsorbent may be separated by known solid-liquid separation means utilizing a sieve, filter paper, or the like.

By allowing the (meth)acrylic acid ester-based synthetic adsorbent to act on the sample liquid in this way, the antimicrobial activity in the test sample is sufficiently reduced. Therefore, even when the adsorbent is removed from the sample liquid and the incubation is carried out without adding the adsorbent to the culture medium, the target microorganism exhibits favorable growth, and thereby high detection precision is obtained. Meanwhile, according to the method of the invention, the (meth)acrylic acid ester-based synthetic adsorbent may also be allowed to further act on the culture medium. In the case where the adsorbent has not been removed from the sample liquid, the instant sample liquid may be added directly to the culture medium. In the case where the adsorbent has been removed from the sample liquid, the instant adsorbent may be separately added to the culture medium. By carrying out the incubation in the culture medium containing the (meth) acrylic acid ester-based synthetic adsorbent, the antimicrobial substances in the culture medium may be adsorbed and removed. A content of the (meth)acrylic acid ester-based synthetic adsorbent in the culture medium is preferably 3 to 20% by mass, and more preferably 5 to 10% by mass. When the content of the (meth)acrylic acid ester-based synthetic adsorbent falls within this range, high detection precision is obtained.

In addition, the (meth)acrylic acid ester-based synthetic adsorbent may also be allowed to act on only the culture medium without being allowed to act on the sample liquid. The method for allowing the adsorbent to act and the additive amount of the adsorbent in the culture medium are the same as those as described above.

In the method of the invention, the medium keeps transparency without being colored despite the presence of the (meth)acrylic acid ester-based synthetic adsorbent. Therefore, it is possible to accurately discriminate colonies formed after the incubation. Furthermore, when the (meth) acrylic acid ester-based synthetic adsorbent is separated and removed from the sample liquid and the resulting sample liquid is added to the culture medium to carry out the incubation, the colonies may be more accurately discriminated. Therefore, for example, even in the plate-count method or the like, it is possible to conduct the colony measurement rapidly and accurately.

While the (meth)acrylic acid ester-based synthetic adsorbent for use in the invention exhibits an adsorption action on a wide range of antimicrobial substances, it has weak adsorption action on nutritional components necessary for the growth of a microorganism. Therefore, the method of the invention may be applied to a wide range of test samples and microorganisms. In addition, the (meth)acrylic acid ester-based synthetic adsorbent does not give influences such as coloration to the medium and is easy for separation and removal, and hence, the test method is not restricted. In consequence, the method of the invention may be applied to the microbial enumeration test of total aerobic microbial count, total yeasts and moulds count, or the like, and the test for the detection of specified microorganisms, such as bile-tolerant gram-negative bacteria, *Escherichia coli*, *Pseudomonas aeruginosa*, *salmonella*, *Staphylococcus aureus*, *Clostridium sporogenes*, and *Candida albicans*, as prescribed in the microbial limit test described in the Japanese Pharmacopoeia. In the case of the test for the detection of specified microorganisms, the (meth)acrylic acid ester-based synthetic adsorbent is allowed to act on the sample liquid and/or the culture medium and subjected to incubate as described above, and then the culture is carried out in a selective medium which is properly used according to the kind of the target microorganism, so that the detection sensitivity is enhanced.

EXAMPLES

The present invention is hereunder described in more detail on the basis of Examples and the like. It is to be noted that the invention is not limited by these Examples and the like at all.

Referential Example 1

Preparation of Microbial Suspension:
Microbial liquids for inoculation to be used for microbial tests were prepared in conformity with the General Tests, Chapter 4.05: Microbial Limit Test in the Japanese Pharmacopoeia 16th edition (revised edition).
(Tester Strains)
*Escherichia coli* (hereinafter abbreviated as "ECO"): IFO (NBRC) No. 3972
*Staphylococcus aureus* (hereinafter abbreviated as "SAU"): IFO (NBRC) No. 13276
*Pseudomonas aeruginosa* (hereinafter abbreviated as "PAE"): IFO (NBRC) No. 13275
*Bacillus subtilis* (hereinafter abbreviated as "BSU"): IFO (NBRC) No. 3134
*Candida albicans* (hereinafter abbreviated as "CAL"): IFO (NBRC) No. 1594
*Aspergillus brasiliensis* (hereinafter abbreviated as "ABR"): NBRC No. 9455
*Clostridium sporogenes* (hereinafter abbreviated as "CSP"): NCTC No. 12935
(Preparation of Microbial Suspension)
50 mL of an SCD medium placed in a 100-mL Erlenmeyer flask was inoculated with one Öse (inoculating loop) of a strain stored in a slant medium. Then, ECO, SAU, and PAE were cultured at 30 to 35° C., and CAL was cultured at 20 to 25° C., thereby preparing microbial suspensions.
As for BSU, the microbial culture solution was heat treated, and the vegetative cells were killed, thereby preparing a spore suspension.
ABR was cultured in a PDA medium at 20 to 25° C., and after the formation of good spores was confirmed, the resulting spores were scraped, thereby preparing a spore solution.
(Preparation of Microbial Liquid for Inoculation)
These microbial suspensions were subjected to serial dilution with a buffered sodium chloride-peptone solution or the like, thereby preparing microbial liquids for inoculation.

Example 1

Examination of Adsorbent (1):
10 g of a sample (Daijokito extract granule, manufactured by Tsumura & Co.) was weighed and added to 90 mL of a buffered sodium chloride-peptone solution containing 10% by mass of an adsorbent (prepared in a 200-mL Erlenmeyer flask), followed by stirring to prepare a sample liquid. DIAION® HP20 (styrene type), DIAION® HP2MG (methacryl type), SEPABEADS® SP700 (styrene type), and SEPABEADS® SP207 (styrene type) (all of which are manufactured by Mitsubishi Chemical Corporation) were used, respectively as the adsorbent. Additionally, in place of 10% by mass of the adsorbent, 10% by mass of skim milk was used for the preparation of a sample liquid in a similar way, and 3% by mass of activated carbon and 5% by mass of activated clay were added to a SCD medium, respectively. Each of the sample liquids was aliquoted and passed through a sieve (made by stainless steel), thereby preparing a 10-fold diluted sample liquid. 10 mL of this 10-fold diluted sample liquid was aliquoted in a test tube. To each test tube, the microbial liquid for inoculation of SAU prepared in Referential Example 1 was added at a concentration of 100 CFU/mL or less, allowed to stand for 2 hours, and then added in a Petri dish, followed by pouring with an SCDLPA medium (manufactured by Nihon Pharmaceutical Co., Ltd.). After incubation at 30 to 35° C. within 5 days, the colony count was carried out. A 10-fold diluted sample liquid having a buffered sodium chloride-peptone solution added thereto (blank) and a 10 mL of the filtered 10% by mass adsorbent-added SCD medium having the microbial solution similarly added thereto (sample-non-added plot) were also subjected to the colony count in the same method, thereby calculating a recovery according to the following equation. The case where the recovery is at least 50% was decided to be adaptive "○"; and the case where the recovery is less than 50% was decided to be non-adaptive "x".

Recovery (%)={($A-B$)×100}/$C$

A: Colony number of each test plot
B: Colony number of blank
C: Colony number of sample-non-added plot

TABLE 1

| Adsorbent | Matrix structure | Decision |
| --- | --- | --- |
| HP20 | Styrene type | ○ |
| HP2MG | Methacryl type | ○ |
| SP700 | Styrene type | X |
| SP207 | Styrene type | X |
| Skim milk | — | X |
| 3% activated carbon/5% activated clay | — | ○ |

In the case of adding HP20 or HP2MG, the recovery was 50% or more, and an antimicrobial substance adsorption ability equal to that of the SCD medium with 3% by mass of activated carbon and 5% by mass of activated clay was exhibited. In addition, whereas the SCD medium with 3% by mass of activated carbon and 5% by mass of activated clay was blackish and opaque, which made colonies difficult to discriminate, the medium with HP20 or HP2MG was so transparent that the discrimination of colonies was facilitated, thereby enabling measuring the colony count rapidly and accurately.

Example 2

Examination of Adsorbent (2):

10 g of a sample (Daijokito extract granule, manufactured by Tsumura & Co.) was weighed and added to 90 mL of an SCD medium in which an adsorbent (HP20 or HP2MG) had been added at a concentration of 3% by mass, 5% by mass, and 10% by mass, respectively (prepared in a 200-mL Erlenmeyer flask), followed by stirring to prepare sample liquids. Each of these sample liquids was aliquoted and passed through a sieve, thereby preparing a 10-fold diluted sample liquid. 10 mL of this 10-fold diluted sample liquid was aliquoted in a test tube. To each of the test plots, the microbial liquid for inoculation of SAU prepared in Referential Example 1 was added at a concentration of 100 CFU/mL or less, allowed to stand for 1 hour, and then added in a Petri dish, followed by pouring with an SODA medium. After incubation at 30 to 35° C. within 5 days, the colony count was carried out. A recovery was calculated in the same method as that in Example 1, thereby deciding the adaptability. In addition, as it sometimes happens that synthetic adsorbents cause difficulty in handling when added in a Petri dish (pipette operation), the difficulty was evaluated according to the following criteria. The results are shown in Table 2.

(Evaluation Criteria of Pipette Handling Properties)

○: There is no problem in handling of the liquid by a general sterilized metering pipette.

x: There is a problem such that weighing is difficult, uniformly aliquot is impossible, clogging is generated, or the like, which hinderes handling.

TABLE 2

| Adsorbent | Content (% by mass) | Decision | Pipette handling properties |
| --- | --- | --- | --- |
| HP20 | 3 | X | X |
|  | 5 | X |  |
|  | 10 | ○ |  |
| HP2MG | 3 | ○ | ○ |
|  | 5 | ○ |  |
|  | 10 | ○ |  |

As for HP2MG, a favorable recovery was exhibited in any of the contents. On the other hand, as for HP20, though a favorable recovery was exhibited at 10% by mass, the recovery was insufficient at 5% by mass or less. In addition, as for HP2MG, the handling properties were favorable even at 10% by mass, whereas as for HP20, the pipette operation was difficult even at 3% by mass.

Example 3

Addition Recovery Test (1):

10 g of each of Kampo extract preparations (Shoseiryuto, Junchoto, Daiokanzoto, and Daijokito, all of which are an extract granule manufactured by Tsumura & Co.), which are confirmed to have high antimicrobial activity, was weighed and added to 90 mL of an SCD medium with 5% or 10% by mass of HP2MG (prepared in a 200-mL Erlenmeyer flask), followed by stirring to prepare sample liquids. Each of these sample liquids was aliquoted and passed through a sieve, thereby preparing a 10-fold diluted sample liquid. 10 mL of this 10-fold diluted sample liquid was aliquoted in a test tube. To each of the test plots, the microbial liquid for inoculation of BSU or PAE prepared in Referential Example 1 was added at a concentration of 100 CFU/mL or less, allowed to stand for 1 hour, and then added in a Petri dish, followed by pouring with an SODA medium. After incubation at 30 to 35° C. within 5 days, the colony count was carried out. A recovery was calculated in the same method as that in Example 1. The case where the recovery is at least 50% was decided to be adaptive "○"; and the case where the recovery is less than 50% was decided to be non-adaptive "x". The results are shown in Table 3.

TABLE 3

| Additive amount of HP2MG | Formulation name | BSU | PAE |
| --- | --- | --- | --- |
| 5% | Shoseiryuto | ○ | ○ |
|  | Junchoto | ○ | ○ |
|  | Daiokanzoto | ○ | ○ |
|  | Daijokito | ○ | ○ |
| 10% | Shoseiryuto | ○ | ○ |
|  | Junchoto | ○ | ○ |
|  | Daiokanzoto | ○ | ○ |
|  | Daijokito | ○ | ○ |

By the addition of HP2MG, all of the tested Kampo extract preparations exhibited a favorable recovery both for BSU and PAE.

Example 4

Examination of Adsorbent (3):

An extract powder of Junchoto and Kampo extract granules of Nijutsuto and Daijokito (all of which are manufactured by Tsumura & Co.), which are confirmed to have antimicrobial activity against BSU, and an extract powder of Junchoto and a Kampo extract granule of Daijokito (all of which are manufactured by Tsumura & Co.), which are confirmed to have antimicrobial activity against SAU, were prepared as test samples for a microbial enumeration test. In addition, Kampo extract powders of Daisaikoto, Daiokanzoto, and Tsudosan (all of which are manufactured by Tsumura & Co.), which are confirmed to have antimicrobial activity against ECO, were prepared as test samples for an *Escherichia coli* test. Each of these Kampo extract preparations was subjected to a microbial enumeration test and an *Escherichia coli* test in conformity with the General Tests, Chapter 4.05: Microbial Limit Test in the Japanese Pharmacopoeia 16th edition (revised edition). As for the Kampo extract granules, 10 g of each of the samples was weighed and added to 90 mL of an SCD medium having 10% by mass of an adsorbent shown in Table 4 added thereto (prepared in a 200-mL Erlenmeyer flask), followed by stirring for 30 minutes to prepare sample liquids. Each of these sample liquids was aliquoted and passed through a sieve, thereby preparing a 10-fold diluted sample liquid. As for the extract powders, 20-fold diluted sample liquids were prepared in the same method, except that 5 g of each of the samples was weighed and added to 95 mL of an SCD medium having 10% by mass of an adsorbent shown in Table 4 added thereto.

(Microbial Enumeration Tests)

To each of the prepared sample liquids, the microbial liquid for inoculation of BSU or SAU prepared in Referential Example 1 was added in an inoculation cell number of 100 CFU/mL or less, followed by stirring. After stirring, the sample liquid was filtered, and the filtrate was dispensed in a Petri dish, followed by pouring with an SCDA medium. After incubation at 30 to 35° C. within 5 days, the colony count of BSU or SAU was carried out. A recovery was calculated in the same method as that in Example 1. The case where the recovery is at least 50% was decided to be adaptive "○"; and the case where the recovery is less than 50% was decided to be non-adaptive "x".

(*Escherichia coli* Test)

To each of the prepared sample liquids, ECO was added in an inoculation cell number of 50 CFU/mL or less and then incubated at 30 to 35° C. for 24 hours. After the incubation, the culture liquid was smeared on a MacConkey agar medium and then incubated at 30 to 35° C. for 24 hours, thereby confirming the growth of ECO. The case where ECO grows was decided to be adaptive "+"; and the case where ECO does not grow was decided to be non-adaptive "−". These results are shown in Table 4.

TABLE 4

| | | | Formulation name | | | | | | |
| --- | --- | --- | --- | --- | --- | --- | --- | --- | --- |
| | | | PuroSorb | | | Amberlite* | | | MUROMAC* |
| | | | PAD350 | PAD550 | PAD950 | XAD4 | FPX 66 | 1180N | SAP9121 |
| | | | | | | Matrix structure | | | |
| | Test strain | | Styrene type | Styrene type | Acryl type | Styrene type | Styrene type | Styrene type | Styrene type |
| Microbial enumeration tests | BSU | Junchoto extract | ○ | X | ○ | ○ | ○ | ○ | X |
| | BSU | Nijutsuto granule | ○ | ○ | ○ | ○ | ○ | ○ | ○ |
| | BSU | Daijokito granule | X | X | ○ | X | ○ | ○ | X |
| | SAU | Junchoto extract | ○ | ○ | ○ | ○ | ○ | ○ | ○ |
| | SAU | Daijokito granule | X | X | ○ | X | ○ | ○ | X |
| *Escherichia coli* test | ECO | Daisaikoto | + | − | + | − | − | − | + |
| | ECO | Daiokanzoto | − | − | + | − | − | − | + |
| | ECO | Tsudosan | − | − | + | − | − | − | + |

| | | | Formulation name | | | | |
| --- | --- | --- | --- | --- | --- | --- | --- |
| | | | MUROMAC* | | LEWATIT* | DIAION* | |
| | | | SAP9690 | WNC6810 | VPOC1600 | HP2MG | SP207 |
| | | | | | Matrix structure | | |
| | Test strain | | Styrene type | Phenol type | Acryl type | Acryl type | Aromatic type |
| Microbial enumeration tests | BSU | Junchoto extract | ○ | X | ○ | ○ | ○ |
| | BSU | Nijutsuto granule | ○ | ○ | ○ | ○ | ○ |
| | BSU | Daijokito granule | ○ | X | ○ | ○ | ○ |
| | SAU | Junchoto extract | ○ | ○ | ○ | ○ | ○ |

TABLE 4-continued

|  |  |  | | | | | |
|---|---|---|---|---|---|---|---|
|  | SAU | Daijokito granule | ○ | X | ○ | ○ | X |
| *Escherichia coli* test | ECO | Daisaikoto | + | + | + | + | − |
|  | ECO | Daiokanzoto | − | − | + | + | − |
|  | ECO | Tsudosan | − | + | + | + | − |

*Registered trademark

In the case where each of PuroSorb PAD950, LEWATIT VPOC1600, and DIAION HP2MG that are a (meth)acrylic acid ester-based synthetic adsorbent had been added to the SCD medium, the growth was confirmed in all of BSU, SAU, and ECO. On the other hand, in the styrene type and other adsorbents, the growth was not confirmed in all of the three microbial species.

Example 5

Microbial Enumeration Tests (Plate-Count Methods):

128 formulations of Kampo extract granules shown in the following Table 5 (all of which are manufactured by Tsumura & Co.) were subjected to a microbial enumeration test using SAU, PAE, BSU, CAL, and ABR, respectively as test microorganisms. As for CAL and ABR, the total aerobic microbial count (TAMC) measurement and the total combined yeasts and moulds count (TYMC) measurement were carried out, and as for SAU, PAE, and BSU, the TAMC measurement was carried out.

10 g of each of the samples was weighed and added to 90 mL of an SCD medium with 10% by mass of HP2MG (prepared in a 200-mL Erlenmeyer flask), followed by stirring to prepare sample liquids. Each of these sample liquids was aliquoted and passed through a sieve, thereby preparing a 10-fold diluted sample liquid. 10 mL of this 10-fold diluted sample liquid was aliquoted in a test tube. Each of the microbial liquids for inoculation prepared in Referential Example 1 was added at a concentration of 100 CFU/mL or less and then allowed to stand for 1 hour.

(TAMC Measurement)

After stirring the inoculated 10-fold diluted sample liquid, 1 mL of the resulting sample liquid was added in a Petri dish and poured with an SCDA medium. The colony count was carried out under incubation condition at 30 to 35° C. within 5 days, and a recovery was calculated in the same method as that in Example 1. The case where the recovery is at least 50% was decided to be adaptive "○"; and the case where the recovery is less than 50% was decided to be non-adaptive "x".

(TYMC Measurement)

After stirring the inoculated 10-fold diluted sample liquid, 1 mL of the resulting sample liquid was added in a Petri dish and poured with an SDA medium. The colony count was carried out under incubation condition at 20 to 25° C. within 5 days, and a recovery was calculated in the same method as that in Example 1. The case where the recovery is at least 50% was decided to be adaptive "○"; and the case where the recovery is less than 50% was decided to be non-adaptive "x". The results are shown in Tables 5 to 8.

TABLE 5

| Formulation name/ | CAL | | ABR | | Formulation name/ | CAL | | ABR | |
|---|---|---|---|---|---|---|---|---|---|
| Microbial species | TAMC | TYMC | TAMC | TYMC | Microbial species | TAMC | TYMC | TAMC | TYMC |
| Kakkonto | ○ | ○ | ○ | ○ | Shigyakusan | ○ | ○ | ○ | ○ |
| Kakkontokasenkyushin'i | ○ | ○ | ○ | ○ | Mokuboito | ○ | ○ | ○ | ○ |
| Otsujito | ○ | ○ | ○ | ○ | Hangebyakujutsutemmato | ○ | ○ | ○ | ○ |
| Anchusan | ○ | ○ | ○ | ○ | Tokishigyakukagoshuyushokyoto | ○ | ○ | ○ | ○ |
| Jumihaidokuto | ○ | ○ | ○ | ○ | Ryokeijutsukanto | ○ | ○ | ○ | ○ |
| Hachimijiogan | ○ | ○ | ○ | ○ | Choreito | ○ | ○ | ○ | ○ |
| Daisaikoto | ○ | ○ | ○ | ○ | Hochuekkito | ○ | ○ | ○ | ○ |
| Shosaikoto | ○ | ○ | ○ | ○ | Rikkunshito | ○ | ○ | ○ | ○ |
| Saikokeishito | ○ | ○ | ○ | ○ | Keishito | ○ | ○ | ○ | ○ |
| Saikokeishikankyoto | ○ | ○ | ○ | ○ | Shichimotsukokato | ○ | ○ | ○ | ○ |
| Saikokaryukotsuboreito | ○ | ○ | ○ | ○ | Chotosan | ○ | ○ | ○ | ○ |
| Hangeshashinto | ○ | ○ | ○ | ○ | Juzentaihoto | ○ | ○ | ○ | ○ |
| Orengedokuto | ○ | ○ | ○ | ○ | Keigairengyoto | ○ | ○ | ○ | ○ |
| Hangekobokuto | ○ | ○ | ○ | ○ | Junchoto | ○ | ○ | ○ | ○ |
| Goreisan | ○ | ○ | ○ | ○ | Yokuininto | ○ | ○ | ○ | ○ |
| Keishikajutsubuto | ○ | ○ | ○ | ○ | Sokeikakketsuto | ○ | ○ | ○ | ○ |
| Shoseiryuto | ○ | ○ | ○ | ○ | Yokukansan | ○ | ○ | ○ | ○ |
| Boiogito | ○ | ○ | ○ | ○ | Makyokansekito | ○ | ○ | ○ | ○ |
| Shohangekabukuryoto | ○ | ○ | ○ | ○ | Gorinsan | ○ | ○ | ○ | ○ |
| Shofusan | ○ | ○ | ○ | ○ | Unseiin | ○ | ○ | ○ | ○ |
| Tokishakuyakusan | ○ | ○ | ○ | ○ | Seijobofuto | ○ | ○ | ○ | ○ |
| Kamishoyosan | ○ | ○ | ○ | ○ | Jizusoippo | ○ | ○ | ○ | ○ |
| Keishibukuryogan | ○ | ○ | ○ | ○ | Keishikashakuyakuto | ○ | ○ | ○ | ○ |
| Keishikaryukotsuboreito | ○ | ○ | ○ | ○ | Tokakujokito | ○ | ○ | ○ | ○ |
| Maoto | ○ | ○ | ○ | ○ | Bofutsushosan | ○ | ○ | ○ | ○ |
| Eppikajutsuto | ○ | ○ | ○ | ○ | Goshakusan | ○ | ○ | ○ | ○ |
| Bakumondoto | ○ | ○ | ○ | ○ | Shakanzoto | ○ | ○ | ○ | ○ |
| Shimbuto | ○ | ○ | ○ | ○ | Kihito | ○ | ○ | ○ | ○ |
| Goshuyuto | ○ | ○ | ○ | ○ | Jinsoin | ○ | ○ | ○ | ○ |
| Ninjinto | ○ | ○ | ○ | ○ | Nyoshinsan | ○ | ○ | ○ | ○ |
| Daiobotampito | ○ | ○ | ○ | ○ | Shakuyakukanzoto | ○ | ○ | ○ | ○ |
| Byakkokaninjinto | ○ | ○ | ○ | ○ | Bukuryoin | ○ | ○ | ○ | ○ |

TABLE 6

| Formulation name/Microbial species | CAL TAMC | CAL TYMC | ABR TAMC | ABR TYMC | Formulation name/Microbial species | CAL TAMC | CAL TYMC | ABR TAMC | ABR TYMC |
|---|---|---|---|---|---|---|---|---|---|
| Kososan | ○ | ○ | ○ | ○ | Sansoninto | ○ | ○ | ○ | ○ |
| Shimotsuto | ○ | ○ | ○ | ○ | Shin'iseihaito | ○ | ○ | ○ | ○ |
| Kambakutaisoto | ○ | ○ | ○ | ○ | Tsudosan | ○ | ○ | ○ | ○ |
| Saikanto | ○ | ○ | ○ | ○ | Unkeito | ○ | ○ | ○ | ○ |
| Choijokito | ○ | ○ | ○ | ○ | Goshajinkigan | ○ | ○ | ○ | ○ |
| Shikunshito | ○ | ○ | ○ | ○ | Ninjin'yoeito | ○ | ○ | ○ | ○ |
| Ryutanshakanto | ○ | ○ | ○ | ○ | Shosaikotokakikyosekko | ○ | ○ | ○ | ○ |
| Kyukikyogaito | ○ | ○ | ○ | ○ | Rikkosan | ○ | ○ | ○ | ○ |
| Makyoyokukanto | ○ | ○ | ○ | ○ | Seishinrenshiin | ○ | ○ | ○ | ○ |
| Heisan | ○ | ○ | ○ | ○ | Choreitogoshimotsuto | ○ | ○ | ○ | ○ |
| Saikoseikanto | ○ | ○ | ○ | ○ | San'oshashinto | ○ | ○ | ○ | ○ |
| Nichinto | ○ | ○ | ○ | ○ | Saireito | ○ | ○ | ○ | ○ |
| Keishininjinto | ○ | ○ | ○ | ○ | Ireito | ○ | ○ | ○ | ○ |
| Yokukansankachimpihange | ○ | ○ | ○ | ○ | Bukuryoingohangekobokuto | ○ | ○ | ○ | ○ |
| Daiokanzoto | ○ | ○ | ○ | ○ | Inchingoreisan | ○ | ○ | ○ | ○ |
| Shimpito | ○ | ○ | ○ | ○ | Ryokyojutsukanto | ○ | ○ | ○ | ○ |
| Tokiinshi | ○ | ○ | ○ | ○ | Ryokankyomishingeninto | ○ | ○ | ○ | ○ |
| Rokumigan | ○ | ○ | ○ | ○ | Orento | ○ | ○ | ○ | ○ |
| Nijutsuto | ○ | ○ | ○ | ○ | Sammotsuogonto | ○ | ○ | ○ | ○ |
| Jidabokuippo | ○ | ○ | ○ | ○ | Hainosankyuto | ○ | ○ | ○ | ○ |
| Seihaito | ○ | ○ | ○ | ○ | Tokikenchuto | ○ | ○ | ○ | ○ |
| Chikujountanto | ○ | ○ | ○ | ○ | Senkyuchachosan | ○ | ○ | ○ | ○ |
| Jiinshihoto | ○ | ○ | ○ | ○ | Keishibukuryogankayokuinin | ○ | ○ | ○ | ○ |
| Jiinkokato | ○ | ○ | ○ | ○ | Mashiningan | ○ | ○ | ○ | ○ |
| Gokoto | ○ | ○ | ○ | ○ | Maobushisaishinto | ○ | ○ | ○ | ○ |
| Saibokuto | ○ | ○ | ○ | ○ | Keihito | ○ | ○ | ○ | ○ |
| Daibofuto | ○ | ○ | ○ | ○ | Daijokito | ○ | ○ | ○ | ○ |
| Ogikenchuto | ○ | ○ | ○ | ○ | Keishikashakuyakudaioto | ○ | ○ | ○ | ○ |
| Shokenchuto | ○ | ○ | ○ | ○ | Inchinkoto | ○ | ○ | ○ | ○ |
| Daikenchuto | ○ | ○ | ○ | ○ | Seishoekkito | ○ | ○ | ○ | ○ |
| Shomakakkonto | ○ | ○ | ○ | ○ | Kamikihito | ○ | ○ | ○ | ○ |
| Tokito | ○ | ○ | ○ | ○ | Kikyoto | ○ | ○ | ○ | ○ |

TABLE 7

| Formulation name/Microbial species | BSU | SAU | PAE | Formulation name/Microbial species | BSU | SAU | PAE |
|---|---|---|---|---|---|---|---|
| Kakkonto | ○ | ○ | ○ | Shigyakusan | ○ | ○ | ○ |
| Kakkontokasenkyushin'i | ○ | ○ | ○ | Mokuboito | ○ | ○ | ○ |
| Otsujito | ○ | ○ | ○ | Hangebyakujutsutemmato | ○ | ○ | ○ |
| Anchusan | ○ | ○ | ○ | Tokishigyakukagoshuyushokyoto | ○ | ○ | ○ |
| Jumihaidokuto | ○ | ○ | ○ | Ryokeijutsukanto | ○ | ○ | ○ |
| Hachimijiogan | ○ | ○ | ○ | Choreito | ○ | ○ | ○ |
| Daisaikoto | ○ | ○ | ○ | Hochuekkito | ○ | ○ | ○ |
| Shosaikoto | ○ | ○ | ○ | Rikkunshito | ○ | ○ | ○ |
| Saikokeishito | ○ | ○ | ○ | Keishito | ○ | ○ | ○ |
| Saikokeishikankyoto | ○ | ○ | ○ | Shichimotsukokato | ○ | ○ | ○ |
| Saikokaryukotsuboreito | ○ | ○ | ○ | Chotosan | ○ | ○ | ○ |
| Hangeshashinto | ○ | ○ | ○ | Juzentaihoto | ○ | ○ | ○ |
| Orengedokuto | ○ | ○ | ○ | Keigairengyoto | ○ | ○ | ○ |
| Hangekobokuto | ○ | ○ | ○ | Junchoto | ○ | ○ | ○ |
| Goreisan | ○ | ○ | ○ | Yokuininto | ○ | ○ | ○ |
| Keishikajutsubuto | ○ | ○ | ○ | Sokeikakketsuto | ○ | ○ | ○ |
| Shoseiryuto | ○ | ○ | ○ | Yokukansan | ○ | ○ | ○ |
| Boiogito | ○ | ○ | ○ | Makyokansekito | ○ | ○ | ○ |
| Shohangekabukuryoto | ○ | ○ | ○ | Gorinsan | ○ | ○ | ○ |
| Shofusan | ○ | ○ | ○ | Unseiin | ○ | ○ | ○ |
| Tokishakuyakusan | ○ | ○ | ○ | Seijobofuto | ○ | ○ | ○ |
| Kamishoyosan | ○ | ○ | ○ | Jizusoippo | ○ | ○ | ○ |
| Keishibukuryogan | ○ | ○ | ○ | Keishikashakuyakuto | ○ | ○ | ○ |
| Keishikaryukotsuboreito | ○ | ○ | ○ | Tokakujokito | ○ | ○ | ○ |
| Maoto | ○ | ○ | ○ | Bofutsushosan | ○ | ○ | ○ |
| Eppikajutsuto | ○ | ○ | ○ | Goshakusan | ○ | ○ | ○ |
| Bakumondoto | ○ | ○ | ○ | Shakanzoto | ○ | ○ | ○ |
| Shimbuto | ○ | ○ | ○ | Kihito | ○ | ○ | ○ |
| Goshuyuto | ○ | ○ | ○ | Jinsoin | ○ | ○ | ○ |
| Ninjinto | ○ | ○ | ○ | Nyoshinsan | ○ | ○ | ○ |
| Daiobotampito | ○ | ○ | ○ | Shakuyakukanzoto | ○ | ○ | ○ |
| Byakkokaninjinto | ○ | ○ | ○ | Bukuryoin | ○ | ○ | ○ |

TABLE 8

| Formulation name/Microbial species | BSU | SAU | PAE | Formulation name/Microbial species | BSU | SAU | PAE |
|---|---|---|---|---|---|---|---|
| Kososan | ○ | ○ | ○ | Sansoninto | ○ | ○ | ○ |
| Shimotsuto | ○ | ○ | ○ | Shin'iseihaito | ○ | ○ | ○ |
| Kambakutaisoto | ○ | ○ | ○ | Tsudosan | ○ | ○ | ○ |
| Saikanto | ○ | ○ | ○ | Unkeito | ○ | ○ | ○ |
| Choijokito | ○ | ○ | ○ | Goshajinkigan | ○ | ○ | ○ |
| Shikunshito | ○ | ○ | ○ | Ninjin'yoeito | ○ | ○ | ○ |
| Ryutanshakanto | ○ | ○ | ○ | Shosaikotokakikyosekko | ○ | ○ | ○ |
| Kyukikyogaito | ○ | ○ | ○ | Rikkosan | ○ | ○ | ○ |
| Makyoyokukanto | ○ | ○ | ○ | Seishinrenshiin | ○ | ○ | ○ |
| Heisan | ○ | ○ | ○ | Choreitogoshimotsuto | ○ | ○ | ○ |
| Saikoseikanto | ○ | ○ | ○ | San'oshashinto | ○ | ○ | ○ |
| Nichinto | ○ | ○ | ○ | Saireito | ○ | ○ | ○ |
| Keishininjinto | ○ | ○ | ○ | Ireito | ○ | ○ | ○ |
| Yokukansankachimpihange | ○ | ○ | ○ | Bukuryoingohangekobokuto | ○ | ○ | ○ |
| Daiokanzoto | ○ | ○ | ○ | Inchingoreisan | ○ | ○ | ○ |
| Shimpito | ○ | ○ | ○ | Ryokyojutsukanto | ○ | ○ | ○ |
| Tokiinshi | ○ | ○ | ○ | Ryokankyomishingeninto | ○ | ○ | ○ |
| Rokumigan | ○ | ○ | ○ | Orento | ○ | ○ | ○ |
| Nijutsuto | ○ | X | ○ | Sammotsuogonto | ○ | ○ | ○ |
| Jidabokuippo | ○ | ○ | ○ | Hainosankyuto | ○ | ○ | ○ |
| Seihaito | ○ | ○ | ○ | Tokikenchuto | ○ | ○ | ○ |
| Chikujountanto | ○ | ○ | ○ | Senkyuchachosan | ○ | ○ | ○ |
| Jiinshihoto | ○ | ○ | ○ | Keishibukuryogankayokuinin | ○ | ○ | ○ |
| Jiinkokato | ○ | ○ | ○ | Mashiningan | ○ | ○ | ○ |
| Gokoto | ○ | ○ | ○ | Maobushisaishinto | ○ | ○ | ○ |
| Saibokuto | ○ | ○ | ○ | Keihito | ○ | ○ | ○ |
| Daibofuto | ○ | ○ | ○ | Daijokito | ○ | ○ | ○ |
| Ogikenchuto | ○ | ○ | ○ | Keishikashakuyakudaioto | ○ | ○ | ○ |
| Shokenchuto | ○ | ○ | ○ | Inchinkoto | ○ | ○ | ○ |
| Daikenchuto | ○ | ○ | ○ | Seishoekkito | ○ | ○ | ○ |
| Shomakakkonto | ○ | ○ | ○ | Kamikihito | ○ | ○ | ○ |
| Tokito | ○ | ○ | ○ | Kikyoto | ○ | ○ | ○ |

Among the 128 Kampo extract formulations and the 896 test plots of seven strains, only one test plot exhibited a recovery of less than 50%, and a very high versatility of the method was confirmed.

Also, it is to be noted that even in the one test plot where the recovery was less than 50%, a slight modification to the test method makes it possible to obtain a recovery of 50% or more.

Example 6

Figure 2:
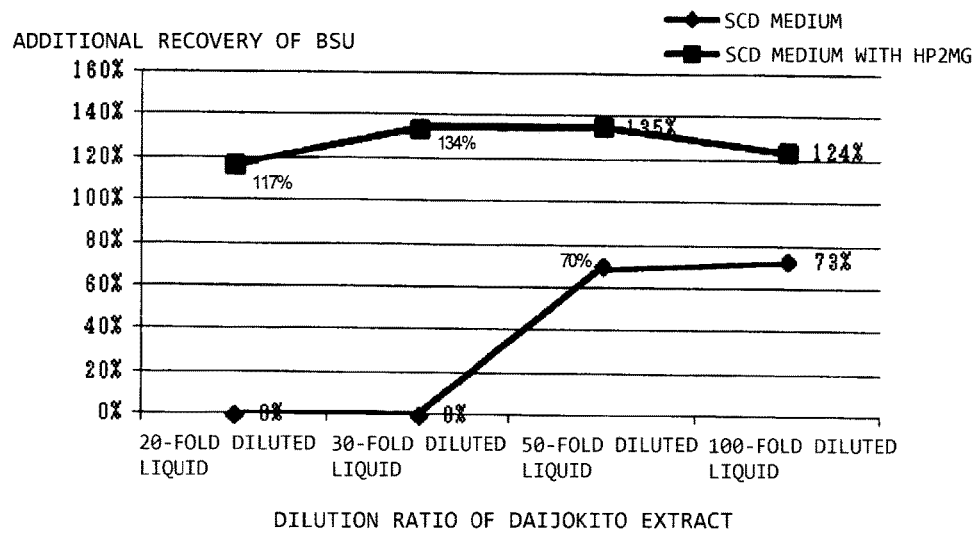
FIG. 2 is a graph plotting an additional recovery of *Bacillus subtilis* with respect to a dilution ratio for Daijokito as a test sample in Example 6.

Addition Recovery Test (2):

An influence of the dilution ratio on the additional recovery was confirmed. 5 g of each of Kampo extract powders (Daiokanzoto and Daijokito, both of which are manufactured by Tsumura & Co.), which are confirmed to have antimicrobial properties against BSU, was weighed and added to 95 mL of an SCD medium or 95 mL of an SCD medium with 10% by mass of HP2MG (prepared in a 200-mL Erlenmeyer flask), followed by stirring to prepare sample liquids having a dilution ratio of 20 times. Similarly, each of the foregoing Kampo extract powders was added to an SCD medium or an SCD medium with 10% by mass of HP2MG in a dilution ratio of 30 times, 50 times, and 100 times, followed by stirring to obtain 30-fold, 50-fold, and 100-fold sample liquids, respectively. To each of the test plots having a dilution ratio of 20 times, 30 times, 50 times, and 100 times, the microbial liquid for inoculation of BSU prepared in Referential Example 1 was added in an inoculation cell number of 100 CFU/mL or less and then allowed to stand for 1 hour. Then, the sample liquid prepared using SCDB with HP2MG was passed through a sieve, and each of the sample liquids was added in a Petri dish and poured with an SODA medium. After incubation at 30 to 35° C. within 5 days, the colony count was carried out. A recovery was calculated in the same method as that in Example 1. The case where the recovery is at least 50% was decided to be adaptive "○"; and the case where the recovery is less than 50% was decided to be non-adaptive "x". The results are shown in Table 9 and FIGS. 1 and 2.

TABLE 9

| Formulation name | Sample liquid | 20-Fold diluted liquid | 30-Fold diluted liquid | 50-Fold diluted liquid | 100-Fold diluted liquid |
|---|---|---|---|---|---|
| Daiokanzoto | SCD medium | X | X | X | ○ |
|  | SCD medium with HP2MG | ○ | ○ | ○ | ○ |
| Daijokito | SCD medium | X | X | ○ | ○ |
|  | SCD medium with HP2MG | ○ | ○ | ○ | ○ |

In the sample liquids prepared in the SCD medium without adding HP2MG, 50% or more of BSU could not be recovered unless the sample liquid was diluted up to 50 or 100 times. On the other hand, in the SCD medium with 10% by mass of HP2MG, the recovery at least 50% was obtained in the dilution of 20 times. In consequence, it was shown that adding 10% by mass of HP2MG enables the microbial enumeration test of the Daiokanzoto extract and the Daijokito extract against BSU to be carried out in a dilution ratio of 30 times or less, and preferably in a dilution ratio of from 20 times to 30 times.

Example 7

Addition Recovery Test (3):

5 g of each of eleven Kampo extract powders (Hangekobokuto, Ninjinto, Hangebyakujutsutemmato, Tokakujokito, Choijokito, Heisan, Daiokanzoto, Chikujountanto, Orento, Mashiningan, and Daijokito, all of which are manufactured by Tsumura & Co.), which are confirmed to have antimicrobial properties against BSU, was weighed and added to 95 mL of an SCD medium or 95 mL of an SCD medium with 10% by mass of HP2MG (prepared in a 200-mL Erlenmeyer flask), followed by stirring to prepare sample liquids. Each of the sample liquids was aliquoted and passed through a sieve, thereby preparing 20-fold diluted sample liquids. To each of the test plots, the microbial liquid for inoculation of BSU prepared in Referential Example 1 was added in an inoculation cell number of 100 CFU/mL or less and then allowed to stand for 1 hour. Then, each of the resulting sample liquids was added in a Petri dish and poured with an SCDA medium. After incubation at 30 to 35° C. within 5 days, the colony count was carried out. A recovery was calculated in the same method as that in Example 1. The case where the recovery is at least 50% was decided to be adaptive "○"; and the case where the recovery is less than 50% was decided to be non-adaptive "x". The results are shown in Table 10.

TABLE 10

| Formulation name | SCD medium | SCD medium with HP2MG |
|---|---|---|
| Hangekobokuto | X | ○ |
| Ninjinto | X | ○ |
| Hangebyakujutsutemmato | X | ○ |
| Tokakujokito | X | ○ |
| Choijokito | X | ○ |
| Heisan | X | ○ |
| Daiokanzoto | X | ○ |
| Chikujountanto | X | ○ |
| Orento | X | ○ |
| Mashiningan | X | ○ |
| Daijokito | X | ○ |
| Sample-non-added plot | ○ | ○ |

As for the sample liquid prepared using the SCD medium, in all of the formulations, the recovery of BSU was less than 50%; whereas in the SCD medium with 10% by mass of HP2MG, in all of the formulations, a recovery of 50% or more was obtained. In consequence, it was shown that adding 10% by mass of HP2MG enables the microbial enumeration test of the Hangekobokuto, Ninjinto, Hangebyakujutsutemmato, Tokakujokito, Choijokito, Heisan, Chikujountanto, Orento, and Mashiningan extract powders against BSU to be carried out in a dilution ratio of 20 times.

Example 8

Test for the Detection of Specified Microorganisms (*Escherichia coli*):
(Direct Culture Method)

5 g of each of Kampo extract powders (Otsujito, Daisaikoto, Shosaikoto, Kamishoyosan, Junchoto, Tokakujokito, Shakuyakukanzoto, Daiokanzoto, Tsudosan, Saireito, and Inchinkoto, all of which are manufactured by Tsumura & Co.), which are confirmed to have antimicrobial activity against *Escherichia coli*, was weighed and added to 95 mL of an SCD medium or 95 mL of an SCD medium with 10% by mass of HP2MG (prepared in a 200-mL Erlenmeyer flask), followed by stirring to prepare 20-fold diluted sample liquids. To each of the prepared sample liquids, the microbial liquid for inoculation of ECO prepared in Referential Example 1 was added in an inoculation cell number of 50 CFU/mL or less and then incubated at 30 to 35° C. for 24 hours. After the incubation, the culture liquid was smeared on a MacConkey agar medium and then incubated at 30 to 35° C. for 24 hours, thereby confirming the growth of ECO. The case where ECO grows was decided to be adaptive "+"; and the case where ECO does not grow was decided to be non-adaptive "−". The results are shown in Table 11.

In the culture in the SCD medium, the growth of ECO was not confirmed in all of the Kampo extract powders; whereas in the SCD medium with 10% HP2MG, the growth was confirmed in, except for the Daiokanzoto formulation, the other ten formulations, thereby exhibiting the capability for detection of ECO.
(Dilution Method)

The Daiokanzoto extract powder in which the growth of ECO by the direct culture method (20-fold dilution) had not been confirmed was treated in an SCD medium with 10% HP2MG, thereby preparing a 20-fold diluted sample liquid. To this sample liquid, ECO was added in an inoculation cell number of 100 CFU/mL or less, and 20 mL of the 20-fold diluted liquid was dispensed in 40 mL of an SCD medium to prepare a 60-fold diluted liquid, followed by incubation at 30 to 35° C. for 24 hours. After the incubation, the culture liquid was smeared on a MacConkey agar medium and then incubated at 30 to 35° C. for 24 hours, thereby confirming the growth of ECO. The case where ECO grows was decided to be adaptive "+"; and the case where ECO does not grow was decided to be non-adaptive "−". The results are shown in Table 11.

TABLE 11

| | Direct culture method | | Dilution method |
|---|---|---|---|
| Formulation name | SCD medium | SCD medium with HP2MG | SCD medium with HP2MG |
| Otsujito | − | + | |
| Daisaikoto | − | + | |
| Shosaikoto | − | + | |
| Kamishoyosan | − | + | |
| Junchoto | − | + | |
| Tokakujokito | − | + | |
| Shakuyakukanzoto | − | + | |
| Daiokanzoto | − | − | + |
| Tsudosan | − | + | |
| Saireito | − | + | |
| Inchinkoto | − | + | |

In consequence, it was shown that adding of 10% by mass of HP2MG enables the test for the detection of specified microorganisms regarding the Otsujito, Daisaikoto, Shosaikoto, Kamishoyosan, Junchoto, Tokakujokito, Shakuyakukanzoto, Tsudosan, Saireito, and Inchinkoto extract powders against ECO to be carried out in a dilution ratio of 20 times. Furthermore, it was shown that even for the Daiokanzoto extract powder in which the growth of ECO was not confirmed by the direct culture method (20-fold dilution), the dilution in the SCD medium in a dilution ratio of 60 times makes it possible to confirm the growth of ECO, thereby enabling the detection.

Example 9

Test for the Detection of Specified Microorganisms (*Clostridia*):

10 g of each of Kampo extract granules (Maoto and Inchinkoto, both of which are manufactured by Tsumura & Co.), which are confirmed to have antimicrobial activity against *Clostridia*, was added to 90 mL of an SCD medium or 90 mL of an SCD medium with 10% by mass of HP2MG, followed by stirring to prepare 10-fold diluted sample liquids. 10 mL of each of the sample liquids was inoculated in 90 mL of a Reinforced Medium for *Clostridia*, and a CSP microbial liquid (BioBall (registered trademark) MultiShot 550, *Clostridium sporogenes*: NCTC12935, manufactured by SYSMEX bioMérieux Co., Ltd.) was added in an inoculation cell number of 50 CFU/mL or less, followed by incubation under an anaerobic condition at 30 to 35° C. for 48 hours. After the incubation, the culture liquid was smeared on a Columbia agar medium and then incubated under an anaerobic condition at 30 to 35° C. for 48 hours, thereby confirming the growth of CSP. The case where CSP grows was decided to be adaptive "+"; and the case where CSP does not grow was decided to be non-adaptive "−". The results are shown in Table 12.

TABLE 12

| Formulation name | Use of SCD medium for sample liquid preparation | Use of SCD medium with HP2MG for sample liquid preparation |
|---|---|---|
| Maoto | − | + |
| Inchinkoto | − | + |

In consequence, as for the test for the detection of specified microorganisms regarding the Maoto and Inchinkoto extract powders against CSP, in the case where the sample liquid was prepared using the SCD medium, the growth of CSP was not confirmed; whereas in the SCD medium with 10% HP2MG, the detection became possible, thereby confirming that the test is feasible.

Example 10

Test for the Detection of Specified Microorganisms (*Escherichia coli*):

5 g of a crude drug (Rhubarb), which is confirmed to have antimicrobial activity against *Escherichia coli*, was weighed and added to 95 mL of an SCD medium or 95 mL of an SCD medium with 10% by mass of HP2MG (prepared in a 200-mL Erlenmeyer flask), followed by stirring to prepare 20-fold diluted sample liquids. Similarly, a crude drug (Rhubarb) was added to an SCD medium or an SCD medium with 10% by mass of HP2MG in a dilution ratio of 100 times and 200 times, followed by stirring to obtain 100-fold and 200-fold sample liquids, respectively. To each of the sample liquids, the microbial liquid for inoculation of ECO prepared in Referential Example 1 was added in an inoculation cell number of 50 CFU/mL or less and then incubated at 30 to 35° C. for 24 hours. After the incubation, the culture liquid was smeared on a MacConkey agar medium and then incubated at 30 to 35° C. for 24 hours, thereby confirming the growth of ECO. The case where ECO grows was decided to be adaptive "+"; and the case where ECO does not grow was decided to be non-adaptive "−". The results are shown in Table 13.

TABLE 13

| Crude drug | Medium | Sample liquid | | | |
| | | 20-Fold diluted liquid | 100-Fold diluted liquid | 200-Fold diluted liquid | Sample-non-added |
|---|---|---|---|---|---|
| Rhubarb | SCD medium with HP2MG | + | + | + | + |
| | SCD medium | − | + | + | + |

In the culture in the SCD medium, the growth of ECO was confirmed in the 100-fold dilution but not in the 20-fold dilution. On the other hand, in the SCD medium with 10% HP2MG, the growth of ECO was confirmed in the 20-fold dilution. In consequence, as for the test for the detection of specified microorganisms regarding Rhubarb against ECO, it was shown that adding 10% by mass of HP2MG enables the detection even without dilution, thereby confirming that the test is feasible.

INDUSTRIAL APPLICABILITY

According to the microorganism detection method of the present invention, it is possible to reduce the influence of a variety of antimicrobial substances and detect microorganisms in a test sample with high precision. In consequence, the microorganism detection method of the invention is extremely useful as a microbial test method of Kampo extract preparations and crude drugs having antimicrobial activity.

The invention claimed is:

1. A method for detecting a microorganism selected from the group consisting of bile-tolerant gram-negative bacteria, *Escherichia coli*, *Pseudomonas aeruginosa*, *Salmonella salmonella*, *Staphylococcus aureus*, *Clostridium sporogenes*, *Candida albicans*, total aerobic microorganism, total yeast, and total mold in a test sample that comprises an antimicrobial substance, the method comprising:
   preparing a sample liquid comprising the test sample, wherein the test sample is a Kampo extract preparation, or a crude drug comprising a plant or animal extract;
   contacting a (meth)acrylic acid ester-based synthetic adsorbent with the sample liquid so that the antimicrobial substance is adsorbed onto the (meth)acrylic acid ester-based synthetic adsorbent; and
   detecting the microorganism based on the growth of the microorganism in the sample liquid.

2. The method according to claim 1, wherein the (meth)acrylic acid ester-based synthetic adsorbent has a modal pore radius of 50 to 1,000 angstrom.

3. The method according to claim 1, wherein the (meth)acrylic acid ester-based synthetic adsorbent is added to the sample liquid.

4. The method according to claim 1, wherein the (meth)acrylic acid ester-based synthetic adsorbent has a concentration of 3 to 20% by mass.

5. The method according to claim 1, wherein the sample liquid and the (meth)acrylic acid ester-based synthetic adsorbent are stirred and mixed for a prescribed time.

6. The method according to claim 5, wherein the prescribed time is 10 to 60 minutes.

7. The method according to claim 1, further comprising:
   removing the (meth)acrylic acid ester-based synthetic adsorbent adsorbed to the antimicrobial substance from the sample liquid after the contacting.

8. The method according to claim 1, wherein the detecting the microorganism based on the growth of the microorganism in the sample liquid comprises:
   adding the sample liquid to a culture medium and incubating the culture medium after the contacting; and
   detecting growth of the microorganism.

9. The method according to claim 1, further comprising after preparing the sample liquid and before the contacting,
   adding the sample liquid to a culture medium.

10. The method according to claim 9, wherein the (meth)acrylic acid ester-based synthetic adsorbent has a modal pore radius 50 to 1,000 angstrom.

11. The method according to claim 9, wherein the (meth)acrylic acid ester-based synthetic adsorbent has a concentration of 3 to 20% by mass in the culture medium.

* * * * *